(12) United States Patent
Ekwuribe

(10) Patent No.: US 6,583,306 B1
(45) Date of Patent: Jun. 24, 2003

(54) METHODS OF ASYMMETRICALLY SYNTHESIZING ENANTIOMERS OF CASODEX, ITS DERIVATIVES AND INTERMEDIATES THEREOF

(75) Inventor: Nnochiri Nkem Ekwuribe, Cary, NC (US)

(73) Assignee: Nobex Corporation, Durham, NC (US)

( * ) Notice: Subject to any disclaimer, the term of this patent is extended or adjusted under 35 U.S.C. 154(b) by 0 days.

(21) Appl. No.: 09/691,621

(22) Filed: Oct. 18, 2000

Related U.S. Application Data
(60) Provisional application No. 60/160,412, filed on Oct. 19, 1999.

(51) Int. Cl.[7] .............................................. C07C 315/00
(52) U.S. Cl. ........................ 558/354; 558/397; 349/296
(58) Field of Search ................................ 558/397, 354; 549/296

(56) References Cited

U.S. PATENT DOCUMENTS

| | | | |
|---|---|---|---|
| 4,636,505 A | 1/1987 | Tucker | 514/256 |
| 4,880,839 A | 11/1989 | Tucker | 514/613 |
| 5,985,868 A | * 11/1999 | Gray | 514/220 |
| 6,019,957 A | 2/2000 | Miller et al. | 424/1.65 |

FOREIGN PATENT DOCUMENTS

| WO | WO98/55153 | 12/1998 |
|---|---|---|

OTHER PUBLICATIONS

Barton et al.; "A Practical Alternative to The Hunsdiecker Reaction" *Tetrahedron Letters*, 24:45 4979–4982 (1983).

Beckwith et al.; "Some Diastereoselective Radical Reactions of Substituted 1,3–Dioxolan–4–ones" *Tetrahedron* 49:36 7871–7882 (1993).

Eggerer et al; "Synthese von Citramalyl–coenzym A und Nachweis seiner enzymatischen Adolspaltung" *Biochemische Zeitschrift* 342 40–53 (1965).

Farines et al.; "Étude de dioxolanones–4: synthése et propriétés physiques" *Bulletin De La Société Chimique De France*, No. 1 332–340 (1970).

Hof et al.; "Synthesis and Lipase–Catalyzed Resolution of 5–(Hydroxymethyl)–1,3–dioxolan–4–ones: Masked Glycerol Analogs as Potential Building Blocks for Pharmaceuticals" *J. Org. Chem.* 61 3423–3427 (1996).

Tucker et al.; "Nonsteroidal Antiandrogens. Synthesis and Structure–Activity Relationships of 3–Substituted Derivatives of 2–Hydroxypropionanilides" *J. Med. Chem.* 31 954–959 (1988).

(List continued on next page.)

*Primary Examiner*—Richard L. Raymond
*Assistant Examiner*—Thomas C McKenzie
(74) *Attorney, Agent, or Firm*—Myers Bigel Sibley & Sajovec, P.A.; William A. Barrett, Esq.

(57) ABSTRACT

Methods of synthesizing pure enantiomers of acylanalides such as Casodex® (bicalutamide) and its derivatives utilizing a compound having a ring structure that, when opened, provides a substituent having the structure of Formula I:

Formula I

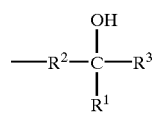

wherein
$R^1$ is alkyl or haloalkyl having up to 4 carbons;
$R^2$ is alkyl having up to 6 carbon atoms; and
$R^3$ is $CH_2OR^4$ where $R^4$ is hydrogen or benzyl, $C(O)CH_3$, or $C(O)OR^5$ where $R^5$ is hydrogen or alkyl;
are disclosed. Methods of synthesizing acylanalides such as Casodex® (bicalutamide) and/or derivatives thereof from a starting material of citramalic acid are also provided.

67 Claims, 3 Drawing Sheets

OTHER PUBLICATIONS

Tucker et al.; "Resolution of the Nonsteroidal Antiandrogen 4'-Cyano-3-[4-fluorophenyl)sulfonyl]-2-hydroxy-2-methyl-3'-(trifluoromethyl)-propionanilide and the Determination of the Absolute Configuration of the Active Enantiomer" *J. Med. Chem.* 31 885–887 (1988).

Zeuner et al.; "Synthese und Polymerisation von 2–Aryl–5–methylen–1,3–dioxolan–4–onen und Arylbis-(5–methylen–1,3–dioxolan–2–yl–4on)en" *J. prakt. Chem.* 337 478–485 (1995).

International Search Report for PCT/US00/41233; mailed Apr. 9, 2001.

Tucker et al., "Resolution of the Nonsteroidal Antiandrogen 4'-Cyano-3-[(4-fluorophenyl)sulfonyl]-2-hydroxy-2-methyl-3'-(trifluoromethyl)-propionanilide and the Determination of the Absolute Configuration of the Active Enantiomer," *J. Med. Chem.* 31:4 885–887 (1988).

* cited by examiner

METHODS OF ASYMMETRICALLY SYNTHESIZING ENANTIOMERS OF CASODEX, ITS DERIVATIVES AND INTERMEDIATES THEREOF

RELATED APPLICATIONS

This application claims priority from N. Ekwuribe, U.S. Provisional Application No. 60/160,412, filed Oct. 19, 1999, the disclosure of which is incorporated by reference herein in its entirety.

FIELD OF THE INVENTION

The present invention relates to methods of synthesizing organic compounds, and more particularly to methods of asymmetrically synthesizing optically active pharmaceutical compounds and their intermediates.

BACKGROUND OF THE INVENTION

Androgen deprivation is a common treatment for persons with prostate cancer. Various non-steroidal antiandrogens are known for use in the treatment of prostate cancer. For example, bicalutamide, which may be among the most commonly used non-steroidal antiandrogens in the world, is typically used in the treatment of prostate cancer. Bicalutamide is commercially available as Casodex® (bicalutamide) from Zeneca Pharmaceuticals.

The chemical name of bicalutamide is N-[4-cyano-3-(trifluoromethyl)phenyl]-3-[(4-fluorophenyl)sulfonyl]-2-hydroxy-2-methyl-propanamide,(+−). The structural formula of bicalutamide is:

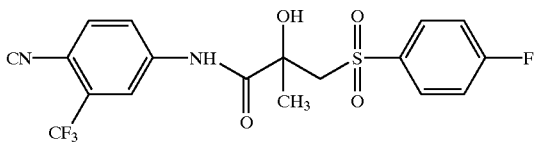

The β-carbon atom in the propanamide is a chiral carbon. As a result, bicalutamide is an optically active compound.

Optically active compounds have the ability to rotate the plane of polarized light. In describing an optically active compound, the prefixes D and L or R and S are used to denote the absolute configuration of the molecule about its chiral center(s). The prefixes d and l or (+) and (−) are used to denote the optical rotation of the compound (i.e., the direction in which a plane of polarized light is rotated by the optically active compound). The l or (−) prefix indicates that the compound is levorotatory (i.e., rotates the plane of polarized light to the left or counterclockwise) while the d or (+) prefix means that the compound is dextrarotatory (i.e., rotates the plane of polarized, light to the right or clockwise). The sign of optical rotation, (−) and (+), is not related to the absolute configuration of the molecule, R and S.

Optically active compounds, such as bicalutamide, exist as a pair of stereoisomers that are identical with the notable exception that they are non-superimposable mirror images of one another. A specific stereoisomer, such as the R isomer, may be referred to as an enantiomer. A mixture of R and S enantiomers may be referred to as a racemic mixture.

Bicalutamide, is presently commercially available as a racemic mixture. The racemic mixture of bicalutamide may be synthesized by various methods including, for example, the methods described in U.S. Pat. No. 4,636,505 to Tucker. Tucker further describes various derivatives and analogs of bicalutamide having antiandrogenic properties. Tucker, however, does not disclose or suggest methods for asymmetrically synthesizing enantiomers of Casodex® (bicalutamide) and/or its intermediates.

U.S. Pat. No. 5,985,868 to Gray proposes synthesizing racemic mixtures of Casidex® (bicalutamide) using methods as described in U.S. Pat. No. 4,636,505 to Tucker, and obtaining the (−) isomer of Casidex® (bicalutamide) by resolution of the enantiomers of Casidex® (bicalutamide) or of intermediates thereto using fractional crystallization or chromatography of diastereomeric esters of chiral acids. Gray notes that other standard methods of resolution such as simple crystallization and chromatographic resolution can also be used. Gray does not disclose or suggest methods of asymmetrically synthesizing enantiomers of Casodex® (bicalutamide) and/or its derivatives and/or intermediates.

In Howard Tucker et al., Resolution of the Nonsteroidal Antiandrogen 4'-Cyano-3-[(4-fluorophenyl)sulfonyl]-2-hydroxy-2-methyl-3'-(trifluoromethyl)-propioanilide and the Determination of the Absolute Configuration of the Active Enantiomer, 31 J. Med. Chem. 885–887 (1988), the authors propose an asymmetric synthesis of (S)-Casodex® (bicalutamide) using the N-methacrylamide of (S)-proline as a starting material. The proposed reaction scheme is as follows:

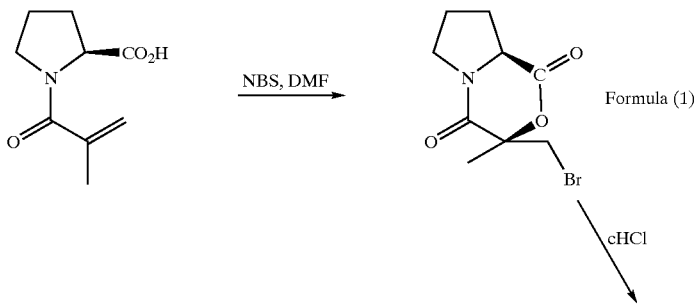

Formula (1)

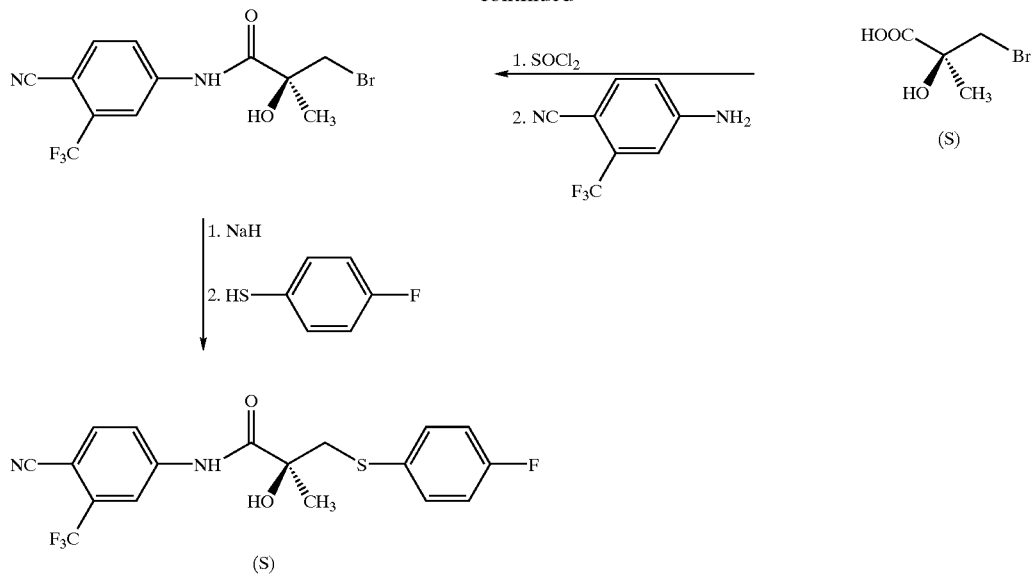

The authors state that this approach is not suitable for the general synthesis of the active enantiomers of analogous anti-androgens, which would require the inaccessible and expensive (R)-proline as a starting material.

U.S. Pat. No. 6,019,957 to Miller et al. proposes an asymmetric synthesis of (R)-Casodex® (bicalutamide) using (R)-proline as a starting material. The proposed reaction scheme is as follows:

As noted above, (R)-proline is an inaccessible and expensive starting material. It would be desirable to provide more cost effective methods for asymmetrically synthesizing enantiomers of Casodex® (bicalutamide) and/or its derivatives and/or intermediates that do not rely on (R)-proline as a starting material.

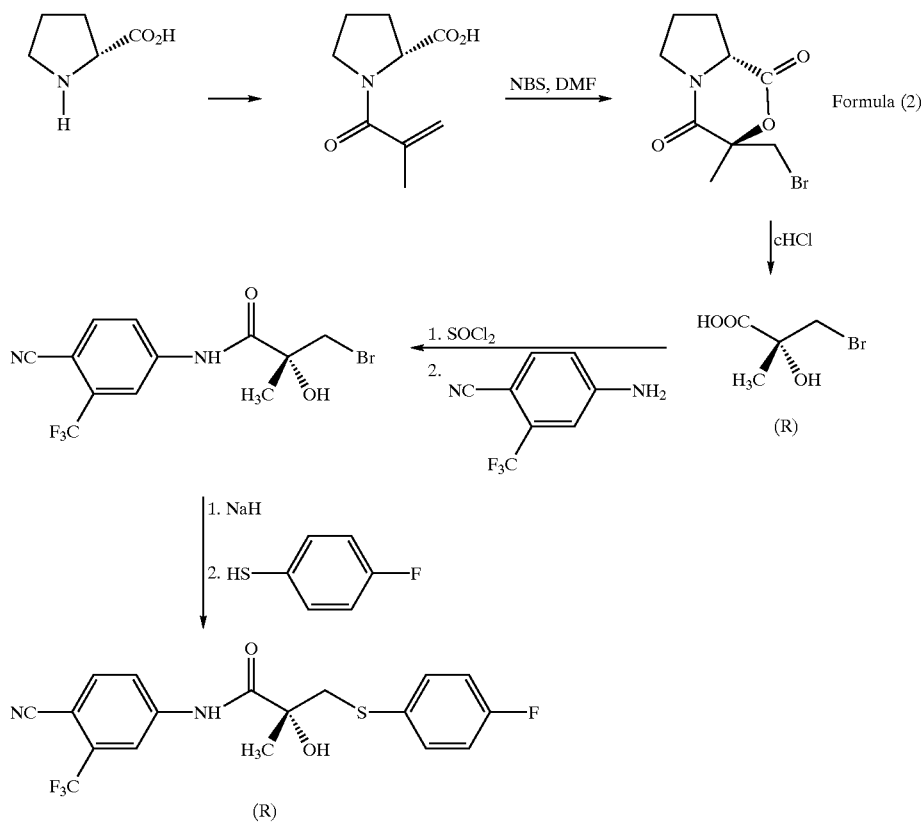

SUMMARY OF THE INVENTION

Embodiments of the present invention provide methods for asymmetrically synthesizing enantiomers of Casodex® (bicalutamide) and/or its intermediates. Asymmetric synthesis methods according to embodiments of the present invention are more cost effective than conventional methods. For example, asymmetric synthesis methods according to embodiments of the present invention react 4-fluorobenzenethiol with the bromolactone of Formula 1 or 2 above. By reacting the 4-fluorobenzenethiol with the bromolactone prior to hydrolyzing the bromolactone instead of hydrolyzing the bromolactone and then reacting the 4-fluorobenzenethiol with the resulting acid as proposed above, improved separation of the reaction products and thus higher yields may be provided. Furthermore, asymmetric synthesis methods according to embodiments of the present invention produce (R)-Casodex® (bicalutamide) and/or its intermediates using (S)-citramalic acid (2-hydroxy-2-methylbutanedioic acid) as a starting material, which may be more cost effective than the conventional scheme, which uses the inaccessible and expensive (R)-proline as a starting material.

According to embodiments of the present invention, methods of asymmetrically synthesizing an enantiomer of an acylanalide such as Casodex® (bicalutamide) or its derivatives are provided. The methods include contacting a compound having a ring structure that, when opened, provides a substituent having the structure of Formula I:

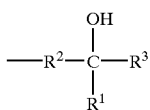

Formula I wherein
- $R^1$ is alkyl or haloalkyl having up to 4 carbons;
- $R^2$ is alkyl having up to 6 carbon atoms; and
- $R^3$ is $CH_2OR^4$ where $R^4$ is hydrogen or benzyl, $C(O)CH_3$, or $C(O)OR^5$ where $R^5$ is hydrogen or alkyl;

with a compound having a structure of Formula II:

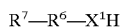

$R^7$—$R^6$—$X^1H$    Formula II wherein
- $R^6$ is a direct link or alkyl having up to 6 carbon atoms;
- $R^7$ is alkyl, alkenyl, hydroxyalkyl or cycloalkyl each of up to 6 carbons; or $R^7$ is phenyl which bears one, two or three substituents independently selected from hydrogen, halogen, nitro, carboxy, carbamoyl and cyano, and alkyl, alkoxy, alkanoyl, alkylthio, alkylsulphinyl, alkylsulphonyl, perfluoroalkyl, perfluoroalkylthio, perfluoroalkylsulphinyl, perfluoroalkylsulphonyl, alkoxycarbonyl and N-alkylcarbamoyl each of up to 4 carbon atoms, and phenyl, phenylthio, phenylsulphinyl and phenylsulphonyl; or $R^7$ is naphthyl; or $R^7$ is a 5- or 6-membered saturated or unsaturated heterocyclic which contains one, two or three heteroatoms selected from oxygen, nitrogen and sulfur, which heterocyclic may be a single ring or may be fused to a benzo-ring, and which heterocyclic is unsubstituted or bears one or two halogen, cyano or amino, or alkyl, alkoxy, alkylthio, alkylsulphinyl or alkylsulphonyl each of up to 4 carbon atoms, or oxy or hydroxy substituents, or which if sufficiently saturated may bear one or two oxo substituents; and $X^1$ is oxygen, sulfur, sulphinyl (—SO—), sulphonyl (—$SO_2$—), imino (—NH—) or alkylimino (—$NR^8$—) where $R^8$ is alkyl having up to 6 carbon atoms;

under conditions sufficient to provide a compound having the structure of Formula III:

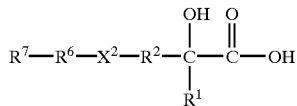

Formula III wherein $X^2$ is oxygen, sulfur, sulphinyl (—SO—), sulphonyl (—$SO_2$—), imino (—NH—), oxidized imino alkylimino (—$NR^8$—) where $R^8$ is alkyl having up to 6 carbon atoms, or oxidized alkylimino. The method further includes treating the compound of Formula III under conditions sufficient to provide a pure enantiomer of Casodex® (bicalutamide) or a pure enantiomer of a Casodex® (bicalutamide) derivative. In preferred embodiments, $R^1$ is methyl, $R^2$ is methylene, $R^6$ is a direct link, $R^7$ is 4-fluorophenyl, $X^1$ is sulfur, the compound of Formula II is 4-fluorobenzenethiol, and $X^2$ is sulphonyl.

In other embodiments according to the present invention, the compound having a ring structure is a compound of Formula IV:

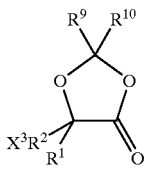

Formula IV wherein
- $R^9$ is hydrogen, or straight, branched or cyclic alkyl;
- $R^{10}$ is straight or branched alkyl, aryl, or $R^{11}X_3^4$, where $R^{11}$ is alkyl and $X^4$ is alkyl, halogen or aryl; and
- $X^3$ is a leaving group.

The compound of Formula IV is contacted with the compound of Formula II under conditions sufficient to provide a compound having the structure of Formula V:

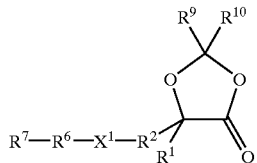

Formula V

In preferred embodiments, $R^1$ is methyl and $R^2$ is methylene. In particularly preferred embodiments, citramalic acid is used as a starting material to provide a compound having the structure of Formula IV. The citramalic acid may be either the (R) or the (S) enantiomer; however, it is preferable to use the (S)-enantiomer of citramalic acid because it may be more readily available and thus, unlike (R)-proline, may be a relatively inexpensive starting material in the synthesis of arylanilides such as Casodex® (bicalutamide) and/or its derivatives. Furthermore, the more active form of Casodex® (bicalutamide) ((R)-Casodex® (bicalutamide)) can be synthesized according to methods of the present invention using (S)-citramalic acid.

In still other embodiments according to the present invention, the compound having a ring structure is a compound of Formula VIII:

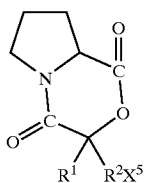

Formula VIII wherein $X^5$ is a leaving group. The compound of Formula VIII is contacted with the compound of Formula II under conditions sufficient to provide a compound having the structure of Formula IX:

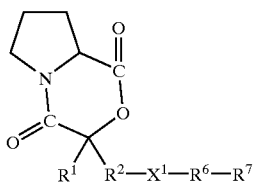

Formula IX

In yet other embodiments of the present invention, the compound having a ring structure is a compound of Formula XI:

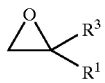

Formula XI

The compound of Formula XI is contacted with the compound of Formula II under conditions sufficient to provide a compound having the structure of Formula XII:

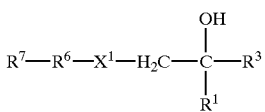

Formula XII

In preferred embodiments, the compound of Formula III is treated with a compound having the structure of Formula XIII:

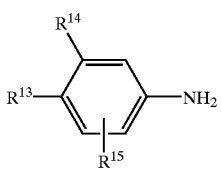

Formula XIII wherein
  $R^{13}$ is cyano, carbamoyl, nitro, fluoro, chloro, bromo, iodo, or hydrogen, or alkyl, alkoxy, alkanoyl, alkylthio, alkylsulphinyl, alkylsulphonyl, perfluoroalkyl, perfluoroalkylthio, perfluoroalkylsulphinyl or perfluoroalkylsulphonyl each having up to 4 carbon atoms, or phenylthio, phenylsulphinyl or phenylsulphonyl;
  $R^{14}$ is cyano, cabamoyl, nitro, fluoro, chloro, bromo or iodo, or alkanoyl, alkylthio, alkylsulphinyl, alkylsulphonyl, perfluoroalkyl, perfluoroalkylthio, perfluoroalkylsulphinyl or perfluoroalkylsulphonyl each of having up to 4 carbon atoms; or phenylthio, phenylsulphinyl or phenylsulphonyl; and
  $R^{15}$ is hydrogen or halogen;
under conditions sufficient to provide a compound of Formula XIV:

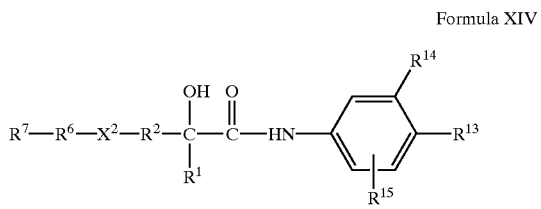

Formula XIV wherein $X^2$ is oxygen, sulfur, sulphinyl (—SO—), sulphonyl (—SO$_2$—), imino (—NH—), oxidized imino alkylimino (—NR$^8$—) where $R^8$ is alkyl having up to 6 carbon atoms, or oxidized alkylimino. In preferred embodiments, the compound of Formula XIII is 4-amino-2-trifluoromethylbenzonitrile, and the compound of Formula XIV is Casodex® (bicalutamide).

Asymmetric synthesis methods according to the present invention may provide pure enantiomers of Casodex® (bicalutamide) and/or its intermediates in a more cost effective manner than conventional methods. For example, as noted above, conventional methods that attempt to provide the more active (R)-enantiomer of Casodex® (bicalutamide) do so either by synthesizing ester derivatives of the racemic mixture and then separating the (R) enantiomer from the (S) enantiomer to produce a Casodex® (bicalutamide) mixture having a higher concentration of (R) enantiomer than (S) enantiomer or by asymmetrically synthesizing the (R)-enantiomer using the inaccessible and expensive (R)-proline as a starting material. By asymmetrically synthesizing the (R) enantiomer of Casodex® (bicalutamide) rather than synthesizing and then separating a racemic mixture, methods according to embodiments of the present invention eliminate the economic waste associated with discarding the (S) enantiomer. Furthermore, according to embodiments of the present invention, (R)-Casodex® (bicalutamide) is asymmetrically synthesized using the readily available (S)-citramalic acid as a starting material rather than the inaccessible and expensive (R)-proline.

DETAILED DESCRIPTION OF PREFERRED EMBODIMENTS

The invention will now be described with respect to preferred embodiments described herein. It should be appreciated however that these embodiments are for the purpose of illustrating the invention, and are not to be construed as limiting the scope of the invention as defined by the claims. As the substituents $R^1$–$R^{15}$, $X^1$–$X^5$ have been defined above, they will not be further defined herein other than to describe preferred substituents for the preferred embodiments.

Embodiments of the present invention provide methods of asymmetrically synthesizing an enantiomer of an acylanilide. Particularly preferred methods provide synthesis routes for Casodex® (bicalutamide) and its derivatives that are more cost effective than conventional preparation techniques.

In a first embodiment, methods of asymmetrically synthesizing an enantiomer of acylanilide comprises contacting a compound having a ring structure that, when opened, provides a substituent having the structure of Formula I:

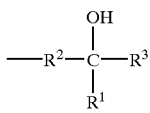

Formula I with a compound having a structure of Formula II:

$R^7$—$R^6$—$X^1$H    Formula II under conditions sufficient to provide a compound having the structure of Formula III:

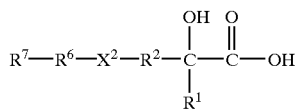

Formula III and, synthesizing the compound of Formula III under conditions sufficient to provide a pure enantiomer of an acylanilide. The pure enantiomer of the acylanilide is preferably a pure enantiomer of Casodex® (bicalutamide) or a derivative thereof. More preferably, the pure enantiomer of the acylanilide is (R)-Casodex® (bicalutamide) or a derivative thereof.

Preferably, $R^1$ and $R^2$ are each lower alkyl having up to 6 carbons. More preferably, $R^1$ is methyl and $R^2$ is methylene. $R^3$ is preferably $CH_2OH$ or $C(O)OH$. Preferably $R^6$ is a direct link (i.e., one or more bonds between $X^1$ and $R^7$). $R^7$ is preferably phenyl which bears one, two or three substituents independently selected from hydrogen, halogen, nitro, carboxy, carbamoyl and cyano, and alkyl, alkoxy, alkanoyl, alkylthio, alkylsulphinyl, alkylsulphonyl, perfluoroalkyl, perfluoroalkylthio, perfluoroalkylsulphinyl, perfluoroalkylsulphonyl, alkoxycarbonyl and N-alkylcarbamoyl each of up to 4 carbon atoms, and phenyl, phenylthio, phenylsulphinyl and phenylsulphonyl. More preferably, $R^7$ is phenyl which bears one, two or three substituents independently selected from hydrogen and halogen. Most preferably, $R^7$ is 4-fluorophenyl. Preferably, $X^1$ is sulfur, sulphinyl, sulphonyl or imino. $X^1$ is more preferably sulfur, sulphinyl, or sulphonyl and is most preferably sulfur. $X^2$ is preferably sulphonyl.

Figure 1:
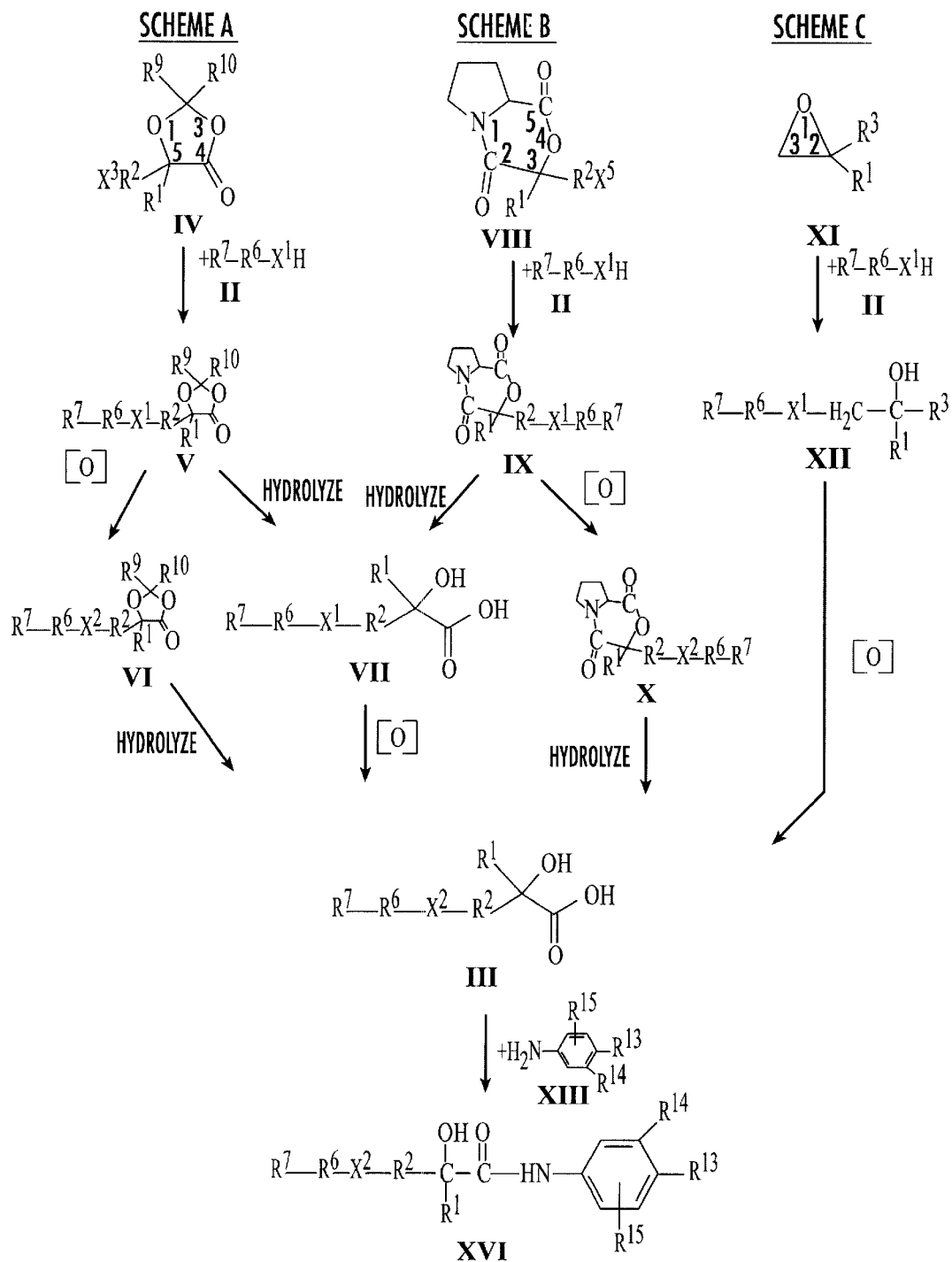
FIG. 1 illustrates a reaction scheme for synthesizing acylanilides such as Casodex® (bicalutamide) that includes attaching the compound of Formula II to compounds having ring structures according to the present invention.

Referring to FIG. 1, embodiments of preferred compounds having ring structures that, when opened, provide substituents having the structure of Formula I:

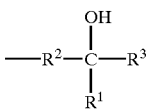

Formula I will now be described. Referring first to Scheme A, the compound having a ring structure is a compound of Formula IV:

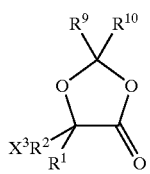

Formula IV

The compound of Formula IV contacts the compound of Formula II under conditions sufficient to provide a compound having the structure of Formula V:

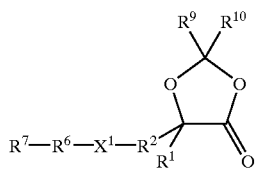

Formula V

As illustrated in FIG. 1, Scheme A, the compound of Formula V may follow one of two separate synthesis routes to provide the compound of Formula III. The compound of Formula V may be oxidized to convert $X^1$ to $X^2$ providing the compound of Formula VI, which may then be hydrolyzed to open the lactone (heterocyclic ring) of Formula VI, providing the compound of Formula III. Alternatively, the compound of Formula V may be hydrolyzed to deprotect the hydroxy acid and provide the compound of Formula VII, which may then be oxidized to convert $X^1$ to $X^2$, providing the compound of Formula III. While the synthesis routes shown in FIG. 1, Scheme A show an oxidation step, it is to be understood that an oxidation step may not be required. For example, an oxidation step may not be required when $X^1$ is sulphonyl, when the oxidation step occurs later in the process (e.g., after the amidation step), or when the acylanilide derivative is not fully oxidized. As will be understood by those skilled in the art, various means may be used to hydrolyze the lactone, including, but not limited to, contacting the lactone of Formula V with an aqueous acid or aqueous base solution. The lactone of Formula V is preferably hydrolyzed using HCl. Those in the art will also understand that a variety of methods and agents may be used to oxidize the compound of Formula V to obtain the compound of Formula III.

Preferably, $R^9$ and $R^{10}$ are selected to allow for hydrolysis of the lactone of Formula IV. $R^9$ is preferably hydrogen, or straight, branched or cyclic lower alkyl. More preferably, $R^9$ is hydrogen. $R^{10}$ is preferably aryl or $R^{11}X_3^4$ where $R^{11}$ is lower alkyl and $X^4$ is lower alkyl, halogen, or aryl. More preferably, $R^{10}$ is benzyl or $R^{11}X_3^4$ where $R^{11}$ is methyl and $X^4$ is methyl, Cl, Br, or phenyl. $X^3$ is a leaving group, as will be understood by those skilled in the art. $X^3$ is preferably halogen, and is more preferably bromine.

Figure 2:
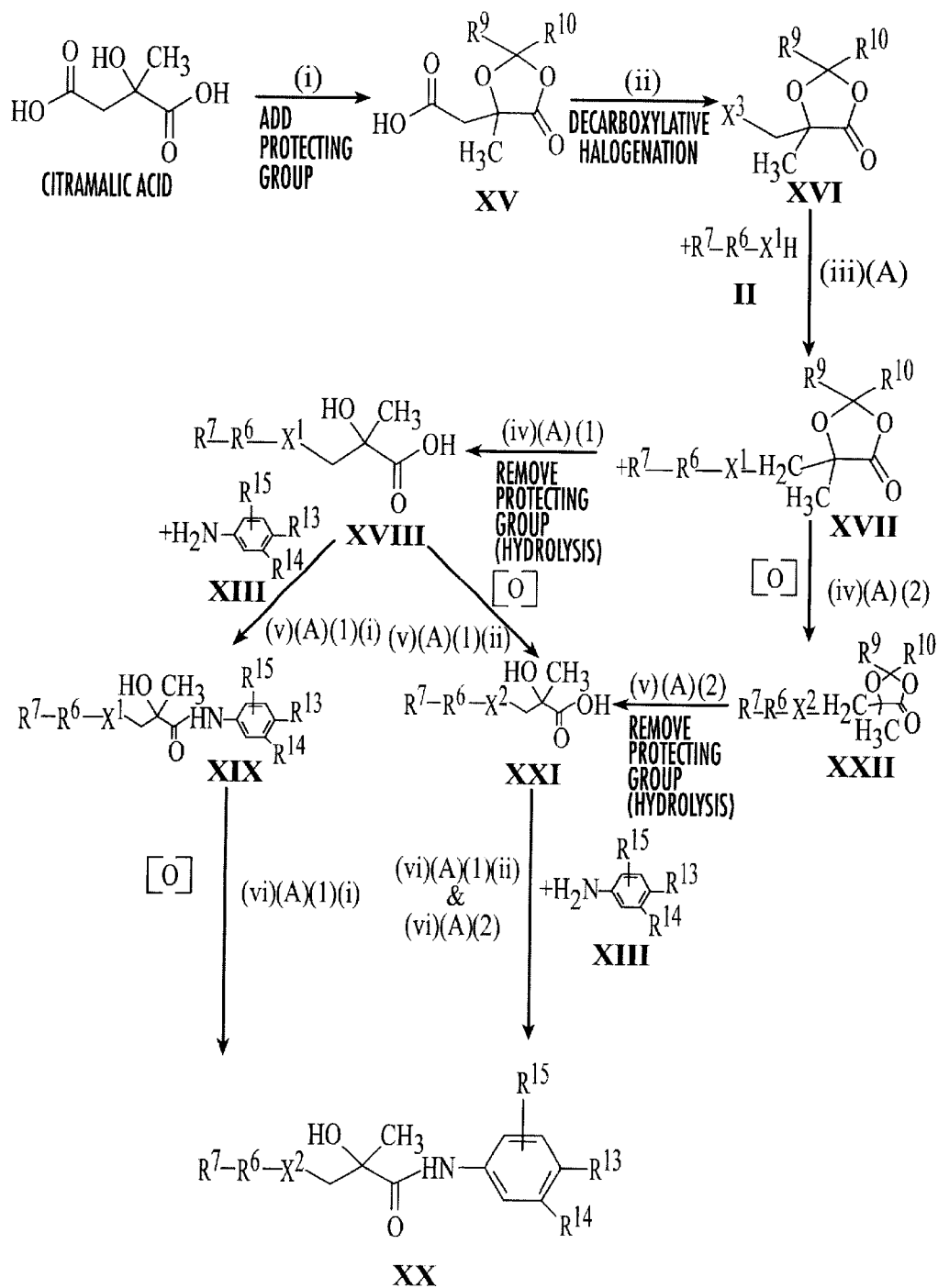
FIG. 2 illustrates three routes for synthesizing acylanilides such as Casodex® (bicalutamide) using citramalic acid as a starting material and attaching the compound of Formula II to the heterocyclic ring structure prior to hydrolyzing the heterocycle according to the present invention.
Figure 3:
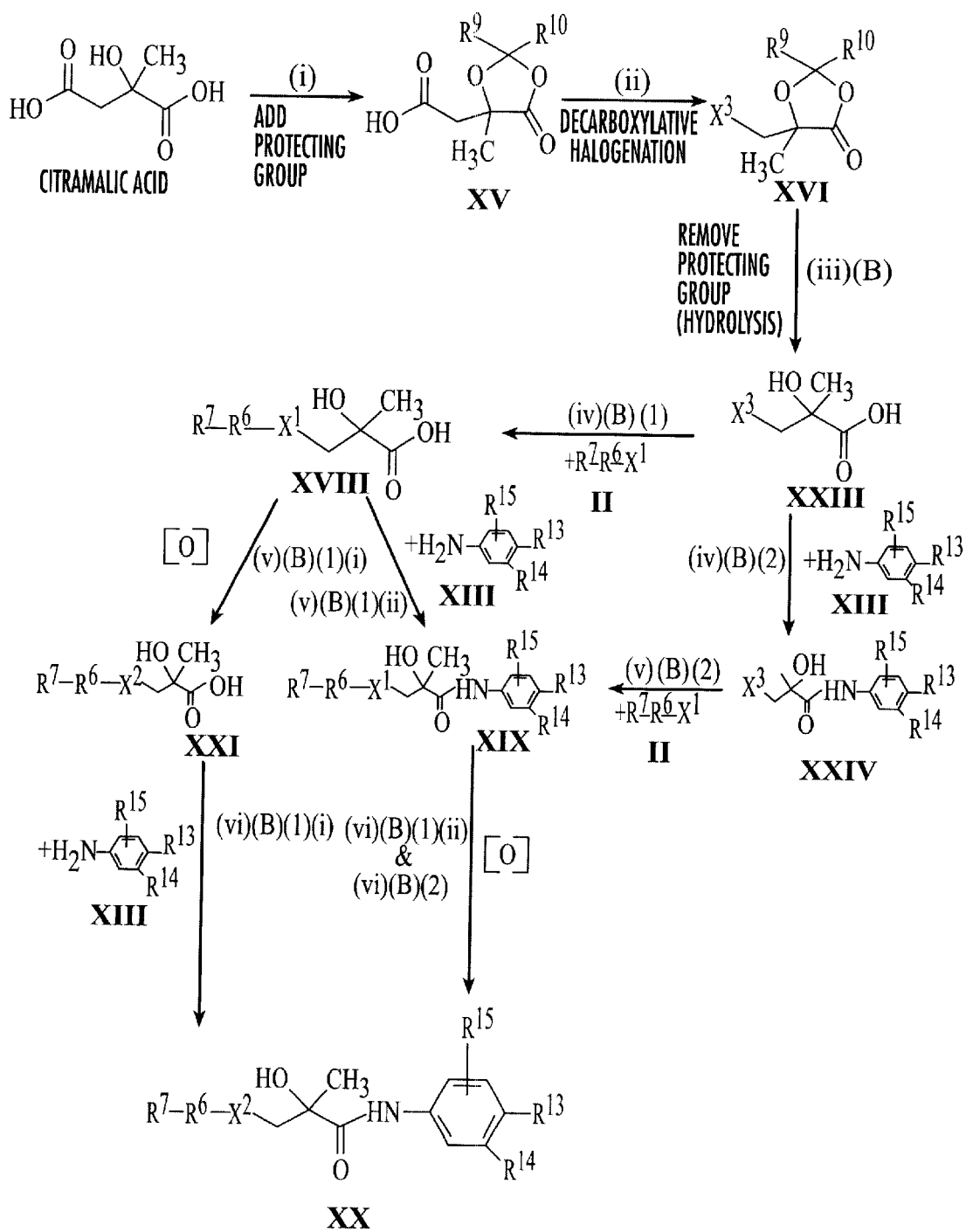
FIG. 3 illustrates three routes for synthesizing acylanilides such as Casodex® (bicalutamide) using citramalic acid as a starting material and hydrolyzing the heterocycle before reacting the citramalic acid derivative with the compound of Formula II according to the present invention.

In a most preferred embodiment, the compound of Formula IV is synthesized from citramalic acid, as illustrated in FIGS. 2 and 3, which will now be described. The following synthesis routes may be employed using (R)-citramalic acid, (S)-citramalic acid, or a racemic mixture thereof as the starting material. Citramalic acid is commercially available from Fluka, a business unit of Sigma-Aldrich Corporation of St. Louis, Mo. For the synthesis of the acylanalide Casodex® (bicalutamide) and its derivatives, it is preferable to use (S)-citramalic acid as the starting material. (S)-citramalic acid may be used as a starting material in methods of the present invention to provide (R)-Casodex® (bicalutamide). (R)-Casodex® (bicalutamide) is believed to be the most active Casodex® (bicalutamide) enantiomer for the treatment of prostate cancer, as well as other androgen related diseases. In sharp contrast to the (R)-proline starting material, which is inaccessible and expensive, (S)-citramalic acid is readily available. Thus, the synthesis methods of the present invention that utilize (S)-citramalic acid as a starting material may be more cost effective than conventional methods that rely on (R)-proline.

The various synthesis routes illustrated in FIGS. 2 and 3 are denoted by the designations next to the reaction arrows. The primary designator (the initial small roman numeral) designates the step number, while the secondary designator (s) (the capital letter, the arabic numeral, and the second small roman numeral) designate the particular route. Synthesis routes having steps that have all of the secondary designators of an earlier step in common have that step in common. For example, in FIG. 2, the steps (vi)(A)(1)(i) and (v)(A)(1)(ii) have all of the secondary designators of step (iv)(A)(1) in common; therefore, step (iv)(A)(1) is a step in both the (A)(1)(i) synthesis route as well as the (A)(1)(ii) synthesis route.

Turning first to FIG. 2, in step (i) a protecting group is added to the citramalic acid to provide the compound of Formula XV. The protecting group is used to protect the hydroxy acid from the decarboxylation step (ii) by forming the dioxolanone of Formula XV. The protecting group may also add molecular weight to the citramalic acid molecule. This larger citramalic acid derivative may be more easily separated after formation of the sulfide as compared to derivatives from which the protecting group is removed prior to formation of the sulfide (e.g., FIG. 3, steps (iii)(B) and (iv)(B)(1)). The protecting group is preferably added by aldol condensation reaction, and more preferably is added by the aldol condensation reaction of bromal and citramalic acid in the presence of sulfuric acid.

In step (ii), the compound of Formula XV undergoes decarboxylative halogenation to provide the compound of Formula XVI. To avoid the heavy metals associated with the Hunsdiecker reaction, it is preferable to use the decarboxylative bromination method proposed by Barton et al. in 24 Tetrahedron Lett. 4979–4982 (1983), which is incorporated herein by reference in its entirety. An example of this bromination method is provided in Example 2, described hereinbelow. While FIGS. 2 and 3 show a step (ii) that is a decarboxylative halogenation step, it will be understood by those skilled in the art that various decarboxylation steps may be used, such as other decarboxylation steps that replace. the carboxylic acid group with a non-halogen leaving group.

In step (iii)(A), the compound of Formula II is added to the compound of Formula XVI to provide the compound of Formula XVII. The compound of Formula II is preferably added by a substitution reaction, as will be understood by those skilled in the art. An example of this substitution reaction is provide in Example 3, described hereinbelow.

Referring now to synthesis route (A)(2), the compound of Formula XVII is oxidized in step (iv)(A)(2) to provide the compound of Formula XXII. The protecting group is then removed from the compound of Formula XXII in step (v)(A)(2), preferably by hydrolysis, to provide the compound of Formula XXI. In step (vi)(A)(2), the compound of Formula XIII is then added to the compound of Formula XXI to provide the acylanilide of Formula XX. The amidation may be performed by various methods as will be understood by those skilled in the art. The amidation is preferably accomplished via in situ generation of the acid chloride. Thionly chloride is the preferred for this procedure.

Synthesis routes (A)(1)(i) and (A)(1(ii) utilize processes similar to those described for synthesis route (A)(2), and will not be further described. Referring to FIG. 3, the synthesis routes (B)(1)(i) and (B)(2) utilize processes similar to those described for synthesis route (A)(2), and will not be further described. Synthesis route (B)(1)(ii) utilizes processes similar to those employed in the other synthesis routes of FIGS. 2 and 3. Synthesis route (B)(1)(ii) is described in some detail in Examples 1–5 hereinbelow. Thus, citramalic acid may be used as a starting material to form the compound of Formula IV:

Formula IV which has a ring structure that, when opened, provides a substituent having the structure of Formula I:

Formula I

Returning to FIG. 1, Scheme B illustrates other methods according to embodiments of the present invention where the compound having a ring structure that, when opened, provides a substituent having the structure of Formula I is a compound having the structure of Formula VIII:

Formula VIII

The compound of Formula VIII may be made, for example, according to the synthesis routes described, for example, in U.S. Pat. No. 6,019,957 to Miller et al. and Howard Tucker et al., Resolution of the Nonsteroidal Antiandrogen 4'-Cyano-3-[(4-fluorophenyl)sulfonyl]-2-hydroxy-2-methyl-3'-(trifluoromethyl)-propioanilide and the Determination of the Absolute Configuration of the Active Enantiomer, 31 J. Med. Chem. 885–887 (1988), the disclosures of which are incorporated herein by reference in their entireties. As noted above, $X^5$ is a leaving group. $X^5$ is preferably halogen and is more preferably bromine.

The compound of Formula VIII contacts the compound of Formula II under conditions sufficient to provide a compound having the structure of Formula IX:

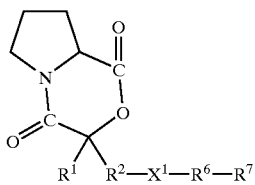

Formula IX

The compound of Formula II is preferably added to the compound of Formula VIII via a substitution reaction, as will be understood by those skilled in the art. For example, a substitution reaction similar to the one described below in Example 3 may be used.

As illustrated in FIG. 1, Scheme B, the compound of Formula IX may follow one of two separate synthesis routes to provide the compound of Formula III. The compound of Formula IX may be hydrolyzed to deprotect the hydroxy acid and provide the compound of Formula VII, which may then be oxidized to convert $X^1$ to $X^2$, providing the compound of Formula III. Alternatively, the compound of Formula IX may be oxidized to convert $X^1$ to $X^2$ providing the compound of Formula X, which may then be hydrolyzed to open the 6-membered heterocyclic ring of Formula X, providing the compound of Formula III. While the synthesis routes shown in FIG. 1, Scheme B show an oxidation step, it is to be understood that an oxidation step may not be required and/or desired. For example, an oxidation step may not be required and/or desired when $X^1$ is sulphonyl, when the oxidation step occurs later in the process (e.g., after the amidation step), or when the acylanilide derivative is not fully oxidized. As will be understood by those skilled in the art, various means may be used to hydrolyze the 6-membered heterocyclic ring, including, but not limited to, contacting the heterocyclic ring of Formula IX with an aqueous acid or aqueous base solution. Preferably, the compound of Formula IX is hydrolyzed using HCl. Those in the art will also understand that a variety of methods and agents may be used to oxidize the compound of Formula IX to obtain the compound of Formula III.

Referring now to FIG. 1, Scheme C, embodiments of methods according to the present invention wherein the compound having a ring structure that, when opened, provides a substituent having the structure of Formula I is a compound of Formula XI:

Formula XI will now be described. The compounds of Formula IX may be made, for example, by chiral epoxidation of alkenes such as alkenols, as will be understood by those skilled in the art. The preferred compound of Formula XI is 2-methyl-1,2-epoxypropanol ($R^1$ is —$CH_3$ and $R^3$ is —$CH_2OH$), which is commercially available from Acros Organics USA of Fair Lawn, N.J. The compound of Formula XI contacts the compound of Formula II under conditions sufficient to provide a compound having the structure of Formula XII:

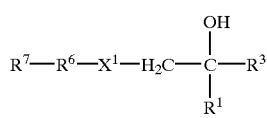

Formula XII

The compound of Formula II is preferably added to the compound of Formula XI via a substitution reaction, as will be understood by those skilled in the art. For example, a substitution reaction similar to the one described below in Example 3 may be used. The compound of Formula XII is then oxidized, as will be understood by those skilled in the art, to convert $X^1$ to $X^2$ and, if necessary, convert $R^3$ to the carboxylic acid to provide the compound of Formula III. While the synthesis routes shown in FIG. 1, Scheme C show an oxidation step, it is to be understood that an oxidation step may not be required and/or desired. For example, an oxidation step may not be required and/or desired when $X^1$ is sulphonyl and/or $R^3$ is C(O)OH.

As illustrated in FIG. 1, the compound of Formula III may be converted to the acylanilide by treating the compound of Formula III with a compound having the structure of Formula XIII:

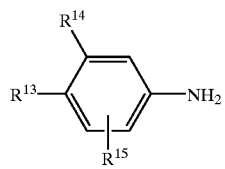

Formula XIII under conditions sufficient to provide a compound of Formula XIV:

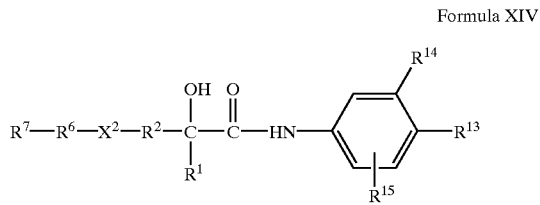

Formula XIV

The amidation may be performed by various methods as will be understood by those skilled in the art. The amidation is preferably accomplished via in situ generation of the acid chloride using thionyl chloride as described above.

$R^{13}$ is preferably cyano, fluoro, chloro, bromo, iodo, or hydrogen. More preferably, $R^{13}$ is cyano, fluoro, chloro, bromo, iodo, and, most preferably, $R^{13}$ is cyano. $R^{14}$ is preferably perfluoroalkyl, perfluoroalkylthio, perfluoroalkylsulphinyl or perfluoroalkylsulphonyl each of having up to 4 carbon atoms. More preferably, $R^{14}$ is perfluoroalkyl, and, most preferably, $R^{14}$ is perfluoromethyl. Most preferably, $R^{15}$ is hydrogen. $X^2$ is preferably sulphonyl.

As described above, pure enantiomers of Casodex® (bicalutamide) and/or its derivatives may be asymmetrically synthesized by methods according to embodiments of the present invention. These enantiomers may be used to treat various diseases. For example, it is preferable to use the (R)-enantiomer of Casodex® (bicalutamide) synthesized by methods of the present invention to treat androgen-dependent diseases, such as prostate cancer. Casodex® (bicalutamide) and/or derivatives thereof synthesized by methods of the present invention may be used in various methods of treatment and pharmaceutical compositions such as, for example, those methods of treatment and pharmaceutical compositions described in U.S. Pat. No. 5,985,868 to Gray, the disclosure of which is incorporated herein by reference in its entirety.

The present invention will now be described with reference to the following examples. It should be appreciated that these examples are for the purposes of illustrating aspects of the present invention, and do not limit the scope of the invention as defined by the claims.

EXAMPLE 1

Synthesizing 4Methyl-5-oxo-2-trihromomethyl-[1,31-dioxolan-4yl]-acetic acid

Bromal (89.1 mmol) and (S)-citramalic acid (74.2 mmol) were cooled to 0° C. in a 125 mL flask under inert atmosphere. Sulfuric acid (25 mL) was added dropwise with stirring. After 2 hrs. the contents were a yellow solution with a white precipitate. The ice bath was removed and the reaction was stirred overnight at room temperture. The dark solution was diluted with ice and extracted 4 times with ethyl acetate. The organic layer was back extracted with water and then was dried with $MgSO_4$. After filtration, the filtrate was concentrated to an oil. The product was obtained as a white solid after crystallization from toluene/hexanes. Yield 60%; mp 151° C. (sublimes); MS ($FAB^+$) 433 (M+Na); $^1H$ NMR ($CDCl_3$): δ 5.77 (s, 1H), 3.06 (d, J=1.79, 2H), 1.74 (s, 3H); $^{13}C$ NMR: δ 174.05, 105.55, 79.63, 43.68, 42.73, 25.38; IR: 3158, 2939, 1825, 1792, 1732; UV: $\lambda_{max}$ 208, $\lambda_{1/2\ max}$ 237. Anal. Calculated for $C_7H_7Br_3O_5$: C, 20.46; H, 1.72. Found: C, 20.89; H, 1.74.

EXAMPLE 2

Synthesizing 5Bromomethyl-5-methyl-2-tribromomethyl-[1,3]dioxolan-4-one

The dioxolanone prepared in Example 1 and 2-mercaptopyridine N-oxide were suspended in $CBrCl_3$. The reaction was heated to reflux and a solution of DCC (dicyclohexylcarbodiamide) in $CBrCl_3$ was added slowly over the course of 30 minutes. The reaction was stirred for an additional hour. The product was purified by silica gel chromatography ($CH_2Cl_2$/hexanes (1/2)) and was obtained as white needles from the same solvents. Yield 65%; mp 110–113° C.; MS ($FAB^+$) no parent ion; $^1H$ NMR δ 5.93 (s, 1H), 3.65 (d, J=1.4, 1H), 1.79 (s, 3H); $^{13}C$ NMR δ 170.58, 105.39, 83.00, 43.51, 35.97, 23.38. IR: 2926, 1825, 1176. UV: $\lambda_{max}$ 210, $\lambda_{1/2max}$ 242. Anal. Calculated for $C_6H_6Br_4O_3$: C, 16.17; H, 1.36. Found: C, 16.38; H, 1.29.

EXAMPLE 3

Synthesizing 3-(4-Fluoro-phenylsulfanyl)-2-hydroxy-2-methyl-propionic acid

The protected hydroxyacid prepared in Example 2 was dissolved in a 1:1 mixture of isopropanol: 1M NaOH. After 3 hrs, the reaction mixture was a solution and no starting material was detectable by TLC (thin-layer chromatography). 4-Fluorobenzenethiol was then added and the reaction was stirred overnight. The reaction was then adjusted to pH 8 with HCl and was extracted 2 times with $CH_2Cl_2$. The aqueous layer was then adjusted to pH 1 and was extracted with $CH_2Cl_2$. The organic layer was concentrated to an oil, which crystallized on standing. The hydroxyacid was either used in the next reaction without further purification or was recrystallized from chloroform/petroleum ether. Yield 80%; mp 73–75° C.; MS ($FAB^+$) 230; $^1H$ NMR: δ 7.43 (dd, J=9.0, J=5.1, 2H), 6.96 (dd, J=9.0, J=9.0, 2H), 3.40 (dd, J=13.8, J=0.9, 1H), 3.15 (dd, J=13.8, J=0.9, 1H), 1.53 (s, 3H); $^{13}CNMR$: δ 180.06, 162.37 (d, J=327.8), 133.93 (d, J=10.6), 130.30, 116.31 (J=29.2), 74.95, 46.22, 25.83; $^{19}F$ NMR: 6-114.21. IR: 3065, 1719. UV: $\lambda_{max}$ 251.

EXAMPLE 4

Synthesizing N-(4-Cyano-3-trifluoromethyl-phenyl)-3-(4-fluoro-phenylsulfanyl)-2-hydroxy-2-methyl-propionamide The hydroxyacid prepared in Example 3 (8.5 mmol) and 4-amino-2-trifluoromethylbenzonitrile (11 mmol) were dissolved in dry DMA (dimethylacetamide) (15 mL) under inert atmosphere. After the solution had been cooled to −10° C., thionyl chloride (10 mmol) was added slowly. The reaction was stirred for 15 min at −10° C., and then the ice bath was removed. After stirring overnight at room temperature, the reaction was diluted with $CH_2Cl_2$ and was extracted one time with saturated $NaHCO_3$. The organic layer was dried with $MgSO_4$ and concentrated. The product was purified by silica gel chromatography (6% ethyl acetate in $CH_2Cl_2$). Yield 45%; MS ($FAB^+$) 399 (M+1); $^1H$ NMR: δ 8.98 (s, 1H), 7.91 (s, 1H), 7.74 (m, 2H), 7.39 (m, 2H), 6.88 (m, 2H), 3.75 (d, J=14.1, 1H), 3.10 (d, J=14.1, 1H), 1.53 (s, 3H); $^{13}C$ NMR: δ 173.10, 160.87, 141.38, 135.90, 133.97, 128.64, 121.84, 117.34, 116.57, 115.68, 104.83, 75.60, 46.07, 26.61; $^{19}F$ NMR: δ−62.74, −113.22. IR: 3357, 3095, 2981, 2232, 1685.

EXAMPLE 5

Synthesizing N-(4cyano-3-trifluoromethyl-phenyl)-3-(4-fluoro-phenylsulfonyl)2-hydroxy-2-methyl-propionamide To a solution of the sulfide prepared in Example 4 (3.19 mmol) in $CH_2Cl_2$ (43 mL) was added mCPBA (meta-chloroperbenzoic acid) (9.57 mmol). After stirring overnight at room temperature, the reaction was diluted with ethyl acetate and extracted two times with $Na_2SO_3$ and $NaHCO_3$. The organic layer was dried with $MgSO_4$ and concentrated. After purification by silica gel chromatography, the product was obtained as white crystals from benzene/petroleum ether. Yield 94%; mp 178° C.; MS ($FAB^+$) 431 (M+1); $^1H$ NMR: 59.16 (s, 1H), 8.00 (d, J=1.5, 1H), 7.88–7.93 (m, 2H), 7.79–7.80 (m, 2H), 7.14–7.20 (m, 2H), 5.02 (s, 1H), 4.00 (d, J=14.5, 1H), 3.51 (d, J=14.5, 1H), 1.61 (s, 3H); $^{13}C$ NMR: δ 171.40, 166.03 ($J_{FC}$=256.7), 141.01, 135.65, 135.01, 133.88 ($J_{FC}$=32.4), 130.78 ($J_{FC}$=9.7), 121.92 ($J_{FC}$=272.0), 121.79, 117.23, 116.75 ($J_{FC}$=22.7), 115.26, 104.82, 74.44, 61.83, 27.80; $^{19}F$ NMR: δ−62.71, −101.63. IR: 3449, 3333, 3104, 2984, 2933, 2231, 1697, 1587, 1517. UV: $\lambda_{max}$ 214, 271. Anal. Calculated for $C_{18}H_{14}F_4N_2O_4S$: C, 50.23; H, 3.28; N, 6.51. Found: C, 50.01; H, 3.26; N, 6.23.

EXAMPLE 6

Biological Data Comparing Pure Enantiomers of Casodex® (bicalutamide) Synthesized by Methods of the Present Invention with Racemic Mixtures of Casodex® (bicalutamide)

The data for dihydrotestosterone are EC50 values. The rest of the data are IC50 values, since the assay is measuring the amount of compound it takes to reduce the testosterone response 50%.

| Compound | Experiment 1 | Experiment 2 |
|---|---|---|
| DHT (Standard) | 0.18 nM | 0.18 nM |
| OH Flut. (Standard) | 19 nM | 41 nM |
| Racemate | 900 nM | 1000 nM |
| (R) | 374 nM | 359 nM |
| (S) | 7700 nM | 11000 nM |

In the drawings and specification, there have been disclosed typical preferred embodiments of the invention and, although specific terms are employed, they are used in a generic and descriptive sense only and not for purposes of limitation, the scope of the invention being set forth in the following claims.

What is claimed is:

1. A method of asymmetrically synthesizing a pure enantiomer of an acylanilide having the structure of Formula XX:

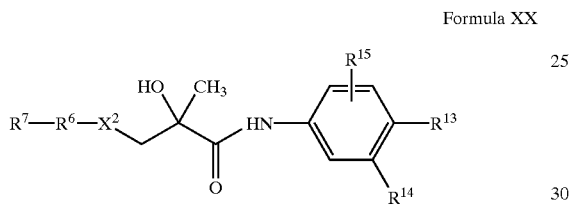

Formula XX wherein
$R^6$ is a direct link or alkyl having up to 6 carbon atoms;
$R^7$ is alkyl, alkenyl, hydroxyalkyl or cycloalkyl each of up to 6 carbons; or $R^7$ is phenyl which bears one, two or three substituents independently selected from hydrogen, halogen, nitro, carboxy, carbamoyl and cyano, and alkyl, alkoxy, alkanoyl, alkylthio, alkylsulphinyl, alkylsulphonyl, perfluoroalkyl, perfluoroalkylthio, perfluoroalkyvsulphinyl, perfluoroalkylsulphonyl, alkoxycarbonyl and N-alkylcarbamoyl each of up to 4 carbon atoms, and phenyl, phenylthio, phenylsulphinyl and phenylsulphonyl; or $R^7$ is naphthyl; or $R^7$ is a 5- or 6-membered saturated or unsaturated heterocyclic which contains one, two or three heteroatoms selected from oxygen, nitrogen and sulfur, which heterocyclic may be a single ring or may be fused to a benzo-ring, and which heterocyclic is unsubstituted or bears one or two halogen, cyano or amino, or alkyl, alkoxy, alkylthio, alkylsulphinyl or alkylsulphonyl each of up to 4 carbon atoms, or oxy or hydroxy substituents, or which if sufficiently saturated may bear one or two oxo substituents;
$X^2$ is oxygen, sulfur, sulphinyl (—SO—), sulphonyl (—SO$_2$—), imino (—NH—), oxidized imino, alkylimino (—NR$^8$—) where $R^8$ is alkyl having up to 6 carbon atoms, or oxidized alkylimino;
$R^{13}$ is cyano, carbamoyl, nitro, fluoro, chloro, bromo, iodo, or hydrogen, or alkyl, alkoxy, alkanoyl, alkylthio, alkylsulphinyl, alkylsulplhonyl, perfluoroalkyl, perfluoroalkylthio, perfluoroalkylsulphinyl or perfluoroalkylsulphonyl each having up to 4 carbon atoms, or phenylthio, phenylsulphinyl or phenylsulphonyl;
$R^{14}$ is cyano, cabamoyl, nitro, fluoro, chloro, bromo or iodo, or alkanoyl, alkylthio, alkylsulphinyl, alkylsulphonyl, perfluoroalkyl, perfluoroalkylthio, perfluoroalkylsulphinyl or perfluoroalkylsulphonyl each of having up to 4 carbon atoms; or phenylthio, phenylsulphinyl or phenylsulphonyl; and
$R^{15}$ is hydrogen or halogen;
the method comprising:
adding a protecting group to the citramalic acid to provide a dioxolanone, wherein the protecting group protects the hydroxy acid of the citramalic acid from decarboxylation; then
decarboxylating the dioxolanone to replace the carboxyl group of the dioxolanone with a leaving group; then
removing the protecting group from the dioxolanone to provide a free carboxylic acid group;
replacing the leaving group with the group —X$^2$R$^6$R$^7$; and
reacting the free carboxylic acid group with a compound having the structure of Formula XIII:

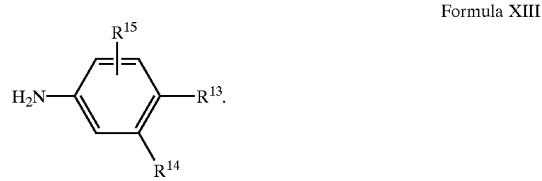

Formula XIII

2. The method according to claim 1, wherein the adding of a protecting group to the citramalic acid comprises:
reacting citramalic acid with a compound having the structure $R^9C(O)R^{10}$ to provide a compound having the structure of Formula XV:

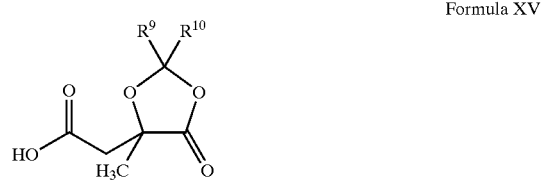

Formula XV wherein
$R^9$ is hydrogen, or straight, branched or cyclic alkyl; and
$R^{10}$ is straight or branched alkyl, aryl, or $R^{11}X_3^4$, where $R^{11}$ is alkylene and $X^4$ is alkyl, halogen or aryl.

3. The method according to claim 2, wherein the reacting of the citramalic acid with the compound having the structure $R^9C(O)R^{10}$ comprises contacting the citramalic acid with bromal in the presence of sulfuric acid.

4. The method according to claim 2, wherein the decarboxylating of the dioxolanone comprises decarboxylating the compound of Formula XV to provide a compound having the structure of Formula XVI:

Formula XVI wherein $X^3$ is a leaving group.

5. The method according to claim 4, wherein the removing of the protective group from the dioxolanone comprises hydrolyzing the compound of Formula XVI in the presence of an aqueous acidic or aqueous basic solution to provide a compound having the structure of Formula XXIII:

6. The method according to claim 5, wherein the replacing of the leaving group comprises reacting a compound having the structure of $R^7$—$R^6$—$X^2$—H with the compound of Formula XXIII to provide a compound having the following structure:

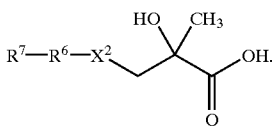

7. The method according to claim 6, wherein the $R^7$—$R^6$—$X^2$—H compound is 4-fluorobenzenethiol.

8. The method according to claim 4, wherein the replacing of the leaving group comprises reacting a compound having the structure of $R^7$—$R^6$—$X^2$—H with the compound of Formula XVI to provide a compound having the following structure:

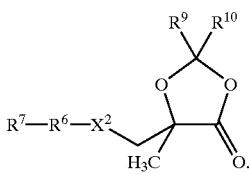

9. The method according to claim 8, wherein the removing of the protective group from the dioxolanone comprises hydrolyzing the compound having the structure:

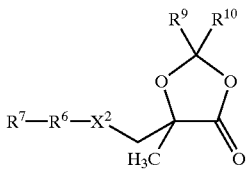

in the presence of an aqueous acidic or aqueous basic solution to provide a compound having the following structure:

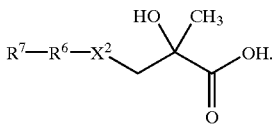

10. The method according to claim 9, wherein the reacting of the free carboxylic acid group with the compound of Formula XIII comprises reacting the compound having the structure:

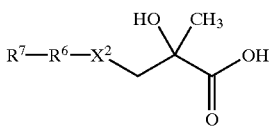

with the compound of Formula XIII to provide the compound of Formula XX.

11. The method according to claim 10, wherein $X^2$ is capable of being oxidized, the method further comprising oxidizing the compound of Formula XX.

12. The method according to claim 5, wherein the reacting of the free carboxylic acid group with the compound of Formula XIII comprises reacting the compound of Formula XXIII with the compound of Formula XIII to provide a compound having the following structure:

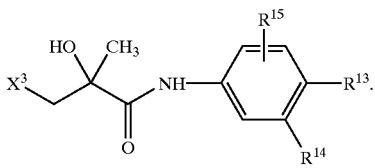

13. The method according to claim 12, wherein the replacing of the leaving group comprises reacting a compound having the structure of $R^7$—$R^6$—$X^2$—H with the compound having the structure:

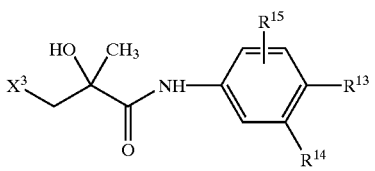

to provide a compound having the structure of Formula XX.

14. The method according to claim 13, wherein $X^2$ is capable of being oxidized, the method further comprising oxidizing the compound of Formula XX.

15. The method according to claim 6, wherein the reacting of the free carboxylic acid group with the compound of Formula XIII comprises reacting the compound having the structure:

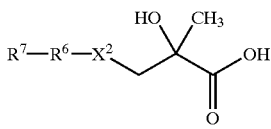

with the compound of Formula XIII to provide the compound of Formula XX.

16. The method according to claim 15, wherein $X^2$ is capable of being oxidized, the method further comprising oxidizing the compound of Formula XX.

17. The method according to claim 16, wherein the oxidizing of the compound of Formula XX comprises contacting the compound of Formula XX with meta-chloroperbenzoic acid.

18. The method according to claim 1, wherein the decarboxylating of the dioxolanone comprises decarboxylatively brominating the dioxolanone with 2-mercaptopyridine N-oxide, dicyclohexylcarbodiamide, and $CBrCl_3$.

19. The method according to claim 1, wherein the removing of the protecting group from the dioxolanone to provide a free carboxylic acid group comprises hydrolyzing the dioxolanone in the presence of an aqueous acidic or aqueous basic solution.

20. The method according to claim 1, wherein the reacting of the free carboxylic acid group with a compound of Formula XIII comprises:

contacting the free carboxylic acid group with thionyl chloride to provide an acid chloride; and contacting the acid chloride with 4-amino-2-trifluoromethylbenzonitrile.

21. The method according to claim 1, wherein $R^7$ is phenyl which bears one, two or three substituents independently selected from hydrogen, halogen, nitro, carboxy, carbamoyl and cyano, and alkyl, alkoxy, alkanoyl, alkylthio, alkylsulphinyl, alkylsulphonyl, perfluoroalkyl, perfluoroalkylthio, perfluoroalkylsulphinyl, perfluoroalkylsulphonyl, alkoxycarbonyl and N-alkylcarbamoyl each of up to 4 carbon atoms, and phenyl, phenylthio, phenylsulphinyl and phenylsulphonyl.

22. The method according to claim 1, wherein $R^7$ is phenyl which bears one, two or three substituents independently selected from hydrogen and halogen.

23. The method according to claim 1, wherein $R^7$ is 4-fluorophenyl.

24. The method according to claim 1, wherein $X^2$ sulphonyl (—$SO_2$—).

25. The method according to claim 1, wherein $R^{13}$ is cyano, fluoro, chloro, bromo, or iodo.

26. The method according to claim 1, wherein $R^{13}$ is cyano.

27. The method according to claim 1, wherein $R^{14}$ is perfluoroalkyl, perfluoroalkylthio, perfluoroalkylsulphinyl or perfluoroalkylsulphonyl each having up to 4 carbon atoms.

28. The method according to claim 1, wherein $R^{14}$ is perfluromethyl.

29. The method according to claim 1, wherein:

$R^7$ is phenyl which bears one, two or three substitutes independently selected from hydrogen, halogen, nitro, carboxy, carbamoyl and cyano, and alkyl, alkoxy, alkanoyl, alkylthio, alkylsulphinyl, alkylsulphonyl, perfluoroalkyl, perfluoroalkylthio, perfluoroalkylsulphinyl, perfluoroalkylsulphonyl, alkoxycarbonyl and N-alkylcarbamoyl each of up to 4 carbon atoms, and phenyl, phenylthio, phenylsulphinyl and phenylsulphonyl;

$R^{13}$ is cyano, fluoro, chloro, bromo, or iodo; and $R^{14}$ is perfluoroalkyl, perfluoroalkylthio, perfluoroalkylsulphinyl or perfluoroalkylsulphonyl each having up to 4 carbon atoms.

30. The method according to claim 1, wherein:

$R^7$ is phenyl which bears one, two or three substituents independently selected from hydrogen and halogen;

$R^{13}$ is cyano, fluoro, chloro, bromo, or iodo; and $R^{14}$ is perfluoroalkyl, perfluoroalkylthio, perfluoroalkylsulphinyl or perfluoroalkylsulphonyl each of having up to 4 carbon atoms.

31. The method according to claim 1, wherein the removing of the protecting group from the lactone occurs after the replacing of the leaving group of the lactone with the group —$X^2R^6R^7$.

32. The method according to claim 1, wherein the reacting of the free carboxylic acid group with a compound of Formula XIII occurs before the replacing of the leaving group of the lactone with the group —$X^2R^6R^7$.

33. A method of asymmetrically synthesizing a pure enantiomer of an acylanilide comprising treating citramalic acid under conditions sufficient to provide the pure enantiomer of an acylanilide, wherein the citramalic acid is (S)-citramalic acid and the pure enantiomer of the acylanilide is (R)-Casodex® (bicalutamide).

34. A method of asymmetrically synthesizing a pure enantiomer of an acylanilide having the structure of Formula XX:

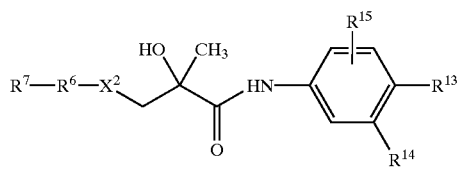

Formula XX wherein $R^6$ is a direct link or alkyl having up to 6 carbon atoms;

$R^7$ is phenyl which bears one, two or three substituents independently selected from hydrogen, halogen, nitro, carboxy, carbamoyl and cyano, and alkyl, alkoxy, alkanoyl, alkylthio, alkylsulphinyl, alkylsulphonyl, perfluoroalkyl, perfluoroalkylthio, perfluoroalkylsulphinyl, perfluoroalkylsulphonyl, alkoxycarbonyl and N-alkylcarbamoyl each of up to 4 carbon atoms, and phenyl, phenylthio, phenylsulphinyl and phenylsulphonyl;

$X^2$ is oxygen, sulfur, sulphinyl (—SO—), sulphonyl (—$SO_2$—), imino (—NH—), oxidized imino, alkylimino (—$NR^8$—) where $R^8$ is alkyl having up to 6 carbon atoms, or oxidized alkylimino;

$R^{13}$ is cyano, fluoro, chloro, bromo, or iodo;

$R^{14}$ is perfluoroalkyl, perfluoroalkylthio, perfluoroalkylsulphinyl or perfluoroalkylsulphonyl each having up to 4 carbon atoms; and $R^{15}$ is hydrogen or halogen;

the method comprising:

adding a protecting group to the citramalic acid to provide a dioxolanone, wherein the protecting group protects the hydroxy acid of the citramalic acid from decarboxylation; then decarboxylating the dioxolanone to replace the carboxyl group of the dioxolanone with a leaving group; then removing the protecting group from the dioxolanone to provide a free carboxylic acid group;

replacing the leaving group with the group —$X^2R^6R^7$; and reacting the free carboxylic acid group with a compound having the structure of

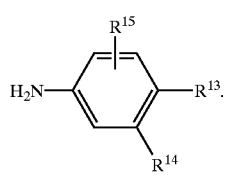

Formula XIII

35. The method according to claim 34, wherein the adding of a protecting group to the citramalic acid comprises:

reacting citramalic acid with a compound having the structure $R^9C(O)R^{10}$ to provide a compound having the structure of Formula XV:

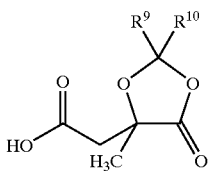

Formula XV wherein
R$^9$ is hydrogen, or straight, branched or cyclic alkyl; and
R$^{10}$ is straight or branched alkyl, aryl, or R$^{11}$X$_3^4$, where R$^{11}$ is alkylene and X$^4$ is alkyl, halogen or aryl.

36. The method according to claim 38, wherein the reacting of the citramalic acid with the compound having the structure R$^9$C(O)R$^{10}$ comprises contacting the citramalic acid with bromal in the presence of sulfuric acid.

37. The method according to claim 35, wherein the decarboxylating of the dioxolanone comprises decarboxylating the compound of Formula XV to provide a compound having the structure of Formula XVI:

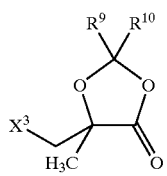

Formula XVI wherein X$^3$ is a leaving group.

38. The method according to claim 37, wherein the removing of the protective group from the dioxolanone comprises hydrolyzing the compound of Formula XVI in the presence of an aqueous acidic or aqueous basic solution to provide a compound having the structure of Formula XXIII:

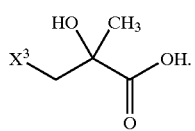

Formula XXIII

39. The method according to claim 48, wherein the replacing of the leaving group comprises reacting a compound having the structure of R$^7$—R$^6$—X$^2$—H with the compound of Formula XXIII to provide a compound having the following structure:

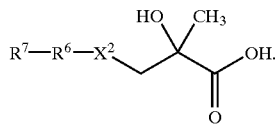

40. The method according to claim 39, wherein the R$^7$—R$^6$—X$^2$—H compound is 4-fluorobenzenethiol.

41. The method according to claim 39, wherein the reacting of the free carboxylic acid group with the compound of Formula XIII comprises reacting the compound having the structure:

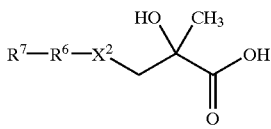

with the compound of Formula XIII to provide the compound of Formula XX.

42. The method according to claim 41, wherein X$^2$ is capable of being oxidized, the method further comprising oxidizing the compound of Formula XX.

43. The method according to claim 42, wherein the oxidizing of the compound of Formula XX comprises contacting the compound of Formula XX with meta-chloroperbenzoic acid.

44. The method according to claim 34, wherein the decarboxylating of the dioxolanone comprises decarboxylatively brominating the dioxolanone with 2-mercaptopyridine N-oxide, dicyclohexylcarbodiamide, and CBrCl$_3$.

45. The method according to claim 34, wherein the removing of the protecting group from the dioxolanone to provide a free carboxylic acid group comprises hydrolyzing the dioxolanone in the presence of an aqueous acidic or aqueous basic solution.

46. The method according to claim 34, wherein the reacting of the free carboxylic acid group with a compound of Formula XIII comprises:
contacting the free carboxylic acid group with thionyl chloride to provide an acid chloride; and
contacting the acid chloride with 4-amino-2-trifluoromethylbenzonitrile.

47. A method of asymmetrically synthesizing a pure enantiomer of an acylanilide having the structure of Formula XX:

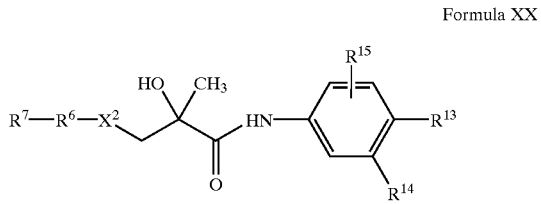

Formula XX wherein
R$^6$ is a direct link or alkyl having up to 6 carbon atoms;
R$^7$ is phenyl which bears one, two or three substituents independently selected from hydrogen and halogen;
X$^2$ is oxygen, sulfur, sulphinyl (—SO—), sulphonyl (—SO$_2$—), imino (—NH—), oxidized imino, alkylimino (—NR$^8$—) where R$^8$ is alkyl having up to 6 carbon atoms, or oxidized alkylimino;
R$^{13}$ is cyano, fluoro, chloro, bromo, or iodo;
R$^{14}$ is perfluoroalkyl, perfluoroalkylthio, perfluoroalkylsulphinyl or perfluoroalkylsulphonyl each having up to 4 carbon atoms; and
R$^{15}$ is hydrogen or halogen;
the method comprising:
adding a protecting group to the citramalic acid to provide a dioxolanone, wherein the protecting group protects the hydroxy acid of the citramalic acid from decarboxylation; then
decarboxylating the dioxolanone to replace the carboxyl group of the dioxolanone with a leaving group; then removing the protecting group from the dioxolanone to provide a free carboxylic acid group;

replacing the leaving group with the group —X²R⁶R⁷; and reacting the free carboxylic acid group with a compound having the structure of Formula XIII:

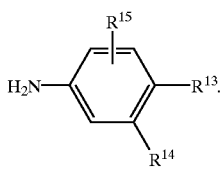

Formula XIII

48. The method according to claim 47, wherein the adding of a protecting group to the citramalic acid comprises:

reacting citramalic acid with a compound having the structure R⁹C(O)R¹⁰ to provide a compound having the structure of Formula XV:

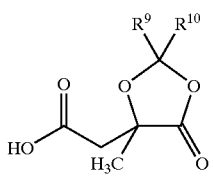

Formula XV wherein

R⁹ is hydrogen, or straight, branched or cyclic alkyl; and

R¹⁰ is straight or branched alkyl, aryl, or R¹¹X₃⁴, where R¹¹ is alkylene and X⁴ is alkyl halogen or aryl.

49. The method according to claim 48, wherein the reacting of the citramalic acid with the compound having the structure R⁹C(O)R¹⁰ comprises contacting the citramalic acid with bromal in the presence of sulfuric acid.

50. The method according to claim 48, wherein the decarboxylating of the dioxolanone comprises decarboxylating the compound of Formula XV to provide a compound having the structure of Formula XVI:

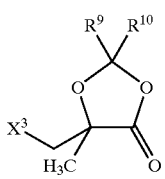

Formula XVI wherein X³ is a leaving group.

51. The method according to claim 50, wherein the removing of the protective group from the dioxolanone comprises hydrolyzing the compound of Formula XVI in the presence of an aqueous acidic or aqueous basic solution to provide a compound having the structure of Formula XXIII:

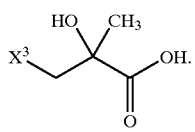

Formula XXIII

52. The method according to claim 51, wherein the replacing of the leaving group comprises reacting a compound having the structure of R⁷—R⁶—X²—H with the compound of Formula XXIII to provide a compound having the following structure:

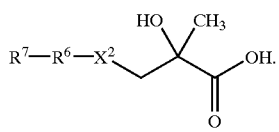

53. The method according to claim 52, wherein the R⁷—R⁶—X²—H compound is 4-fluorobenzenethiol.

54. The method according to claim 52, wherein the reacting of the free carboxylic acid group with the compound of Formula XIII comprises reacting the compound having the structure:

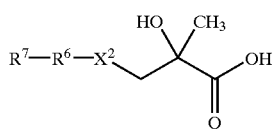

with the compound of Formula XIII to provide the compound of Formula XX.

55. The method according to claim 54, wherein X² is capable of being oxidized, the method further comprising oxidizing the compound of Formula XX.

56. The method according to claim 55, wherein the oxidizing of the compound of Formula XX comprises contacting the compound of Formula XX with meta-chloroperbenzoic acid.

57. The method according to claim 47, wherein the decarboxylating of the dioxolanone comprises decarboxylatively brominating the dioxolanone with 2-mercaptopyridine N-oxide, dicyclohexylcarbodiamide, and CBrCl₃.

58. The method according to claim 47, wherein the removing of the protecting group from the dioxolanone to provide a free carboxylic acid group comprises hydrolyzing the dioxolanone in the presence of an aqueous acidic or aqueous basic solution.

59. The method according to claim 47, wherein the reacting of the free carboxylic acid group with a compound of Formula XIII comprises:

contacting the free carboxylic acid group with thionyl chloride to provide an acid chloride; and contacting the acid chloride with 4-amino-2-trifluoromethylbenzonitrile.

60. A method of asymmetrically synthesizing a pure enantiomer of an acylanilide comprising:

reacting citramalic acid with a compound having the structure R⁹C(O)R¹⁰ to provide a compound having the structure of Formula XV:

Formula XV

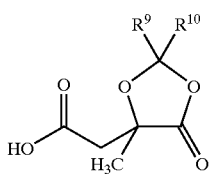

wherein
R⁹ is hydrogen, or straight, branched or cyclic alkyl; and
R¹⁰ is straight or branched alkyl, aryl, or $R^{11}X_3^4$, where $R^{11}$ is alkylene and $X^4$ is alkyl, halogen or aryl;
decarboxylating the compound of Formula XV to provide a compound having the structure of Formula XVI:

Formula XVI

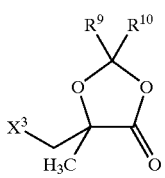

wherein $X^3$ is a leaving group;
hydrolyzing the compound of Formula XVI to provide a compound having the structure of Formula XXIII:

Formula XXIII

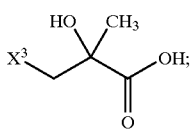

reacting the compound of Formula XXIII with a compound having the following structure:

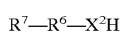

wherein
$X^2$ is oxygen, sulfur, sulphinyl (—SO—), sulphonyl (—SO₂—), imino (—NH—) or alkylimino (—NR⁸—) where R⁸ is alkyl having up to 6 carbon atoms;
R⁶ is a direct link or alkyl having up to 6 carbon atoms;
R⁷ is alkyl, alkenyl, hydroxyalkyl or cycloalkyl each of up to 6 carbons; or R⁷ is phenyl which bears one, two or three substituents independently selected from hydrogen, halogen, nitro, carboxy, carbamoyl and cyano, and alkyl, alkoxy, alkanoyl, alkylthio, alkylsulphinyl, alkylsulphonyl, perfluoroalkyl, perfluoroalkylthio, perfluoroalkylsulphinyl, perfluoroalkylsulphonyl, alkoxycarbonyl and N-alkylcarbamoyl each of up to 4 carbon atoms, and phenyl, phenylthio, phenylsulphinyl and phenylsulphonyl; or R⁷ is naphthyl; or R⁷ is a 5- or 6-membered saturated or unsaturated heterocyclic which contains one, two or three heteroatoms selected from oxygen, nitrogen and sulfur, which heterocyclic may be a single ring or may be fused to a benzo-ring, and which heterocyclic is unsubstituted or bears one or two halogen, cyano or amino, or alkyl, alkoxy, alkylthio, alkylsulphinyl or alkylsulphonyl each of up to 4 carbon atoms, or oxy or hydroxy substituents, or which if sufficiently saturated may bear one or two oxo substituents;
to provide a compound having the following structure:

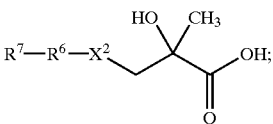

reacting the free carboxylic acid group of the compound with a compound having the structure of Formula XIII:

Formula XIII

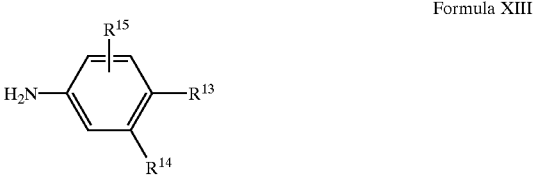

wherein
R¹³ is cyano, carbamoyl, nitro, fluoro, chloro, bromo, iodo, or hydrogen, or alkyl, alkoxy, alkanoyl, alkylthio, alkylsulphinyl, alkylsulphonyl, perfluoroalkyl, perfluoroalkylthio, perfluoroalkylsulphinyl or perfluoroalkylsulphonyl each having up to 4 carbon atoms, or phenylthio, phenylsulphinyl or phenylsulphonyl;
R¹⁴ is cyano, cabamoyl, nitro, fluoro, chloro, bromo or iodo, or alkanoyl, alkylthio, alkylsulphinyl, alkylsulphonyl, perfluoroalkyl, perfluoroalkylthio, perfluoroalkylsulphinyl or perfluoroalkylsulphonyl each having up to 4 carbon atoms; or phenylthio, phenylsulphinyl or phenylsulphonyl; and
R¹⁵ is hydrogen or halogen;
to provide a compound having the structure of Formula XX:

Formula XX

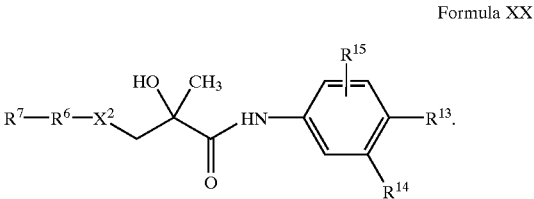

61. The method according to claim 60, wherein the reacting of the citramalic acid with a compound having the structure $R^9C(O)R^{10}$ comprises contacting the citramalic acid with bromal in the presence of sulfuric acid.

62. The method according to claim 60, wherein the decarboxylating of the compound of Formula XV comprises decarboxylatively brominating the compound of Formula XV with 2-mercaptopyridine N-oxide, dicyclohexylcarbodiamide, and CBrCl₃.

63. The method according to claim 60, wherein the hydrolyzing of the compound of Formula XVI comprises contacting the compound of Formula XVI with HCl.

64. The method according to claim 60, wherein the reacting of the free carboxylic acid group with a compound of Formula XIII comprises:
contacting the free carboxylic acid group with thionyl chloride to provide an acid chloride; and
contacting the acid chloride with 4-amino-2-trifluoromethylbenzonitrile.

65. The method according to claim 603, wherein $X^2$ is capable of being oxidized, the method further comprising oxidizing the compound of Formula XX.

66. A method of asymmetrically synthesizing a pure enantiomer of an acylanilide or a derivative thereof comprising:

reacting citramalic acid with a compound having the structure $R^9C(O)R^{10}$ to provide a compound having the structure of Formula XV:

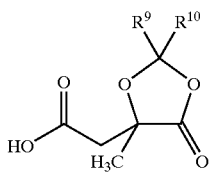

Formula XV wherein
$R^9$ is hydrogen, or straight, branched or cyclic alkyl; and
$R^{10}$ is straight or branched alkyl, aryl, or $R^{11}X_3^4$, where $R^{11}$ is alkylene and $X^4$ is alkyl, halogen or aryl;

decarboxylating the compound of Formula XV to provide a compound having the structure of Formula XVI:

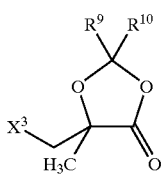

Formula XVI wherein $X^3$ is a leaving group;

hydrolyzing the compound of Formula XVI to provide a compound having the structure of Formula XXIII:

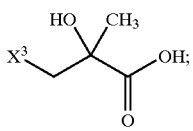

Formula XXIII reacting the compound of Formula XXIII with a compound having the structure of Formula XIII:

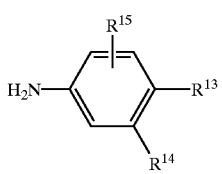

Formula XIII wherein
$R^{13}$ is cyano, carbamoyl, nitro, fluoro, chloro, bromo, iodo, or hydrogen, or alkyl, alkoxy, alkanoyl, alkylthio, alkylsulphinyl, alkylsulphonyl, perfluoroalkyl, perfluoroalkylthio, perfluoroalkylsulphinyl or perfluoroalkylsulphonyl each having up to 4 carbon atoms, or phenylthio, phenylsulphinyl or phenylsulphonyl;

$R^{14}$ is cyano, cabamoyl, nitro, fluoro, chloro, bromo or iodo, or alkanoyl, alkylthio, alkylsulphinyl, alkylsulphonyl, perfluoroalkyl, perfluoroalkylthio, perfluoroalkylsulphinyl or perfluoroalkylsulphonyl each having up to 4 carbon atoms; or phenylthio, phenylsulphinyl or phenylsulphonyl; and $R^{15}$ is hydrogen or halogen;

to provide an aniline compound having the following structure:

reacting the aniline compound with a compound having the following structure:

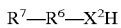

$R^7$—$R^6$—$X^2H$ wherein
$X^2$ is oxygen, sulfur, sulphinyl (—SO—), sulphonyl (—SO$_2$—), imino (—NH—) or alkylimino (—NR$^8$—) where $R^8$ is alkyl having up to 6 carbon atoms;

$R^6$ is a direct link or alkyl having up to 6 carbon atoms;

$R^7$ is alkyl, alkenyl, hydroxyalkyl or cycloalkyl each of up to 6 carbons; or $R^7$ is phenyl which bears one, two or three substituents independently selected from hydrogen, halogen, nitro, carboxy, carbamoyl and cyano, and alkyl, alkoxy, alkanoyl, alkylthio, alkylsulphinyl, alkylsulphonyl, perfluoroalkyl, perfluoroalkylthio, perfluoroalkylsulphinyl, perfluoroalkylsulphonyl, alkoxycarbonyl and N-alkylcarbamoyl each of up to 4 carbon atoms, and phenyl, phenylthio, phenylsulphinyl and phenylsulphonyl; or $R^7$ is naphthyl; or $R^7$ is a 5- or 6-membered saturated or unsaturated heterocyclic which contains one, two or three heteroatoms selected from oxygen, nitrogen and sulfur, which heterocyclic may be a single ring or may be fused to a benzo-ring, and which heterocyclic is unsubstituted or bears one or two halogen, cyano or amino, or alkyl, alkoxy, alkylthio, alkylsulphinyl or alkylsulphonyl each of up to 4 carbon atoms, or oxy or hydroxy substituents, or which if sufficiently saturated may bear one or two oxo substituents;

to provide a compound having the structure of Formula XX:

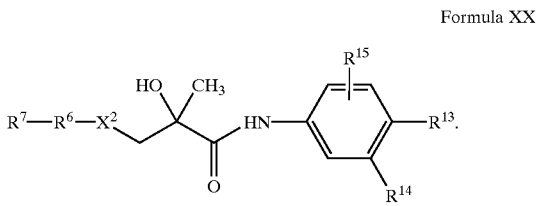

Formula XX

67. A method of asymmetrically synthesizing a pure enantiomer of an acylanilide or a derivative thereof comprising:

reacting citramalic acid with a compound having the structure $R^9C(O)R^{10}$ to provide a compound having the structure of Formula XV:

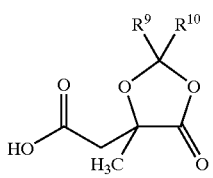

Formula XV wherein
R$^9$ is hydrogen, or straight, branched or cyclic alkyl; and
R$^{10}$ is straight or branched alkyl, aryl, or R$^{11}$X$_3^4$, where R$^{11}$ is alkylene and X$^4$ is alkyl, halogen or aryl;
decarboxylating the compound of Formula XV to provide a compound having the structure of Formula XVI:

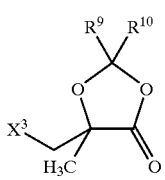

Formula XVI wherein X$^3$ is a leaving group;
reacting the compound of Formula XVI with a compound having the following structure:

R$^7$—R$^6$—X$^2$H wherein
X$^2$ is oxygen, sulfur, sulphinyl (—SO—), sulphonyl (—SO$_2$—), imino (—NH—) or alkylimino (—NR$^8$—) where R$^8$ is alkyl having up to 6 carbon atoms;
R$^6$ is a direct link or alkyl having up to 6 carbon atoms;
R$^7$ is alkyl, alkenyl, hydroxyalkyl or cycloalkyl each of up to 6 carbons; or R$^7$ is phenyl which bears one, two or three substituents independently selected from hydrogen, halogen, nitro, carboxy, carbamoyl and cyano, and alkyl, alkoxy, alkanoyl, alkylthio, alkylsulphinyl, alkylsulphonyl, perfluoroalkyl, perfluoroalkylthio, perfluoroalkylsulphinyl, perfluoroalkylsulphonyl, alkoxycarbonyl and N-alkylcarbamoyl each of up to 4 carbon atoms, and phenyl, phenylthio, phenylsulphinyl and phenylsulphonyl; or R$^7$ is naphthyl; or R$^7$ is a 5- or 6-membered saturated or unsaturated heterocyclic which contains one, two or three heteroatoms selected from oxygen, nitrogen and sulfur, which heterocyclic may be a single ring or may be fused to a benzo-ring, and which heterocyclic is unsubstituted or bears one or two halogen, cyano or amino, or alkyl, alkoxy, alkylthio, alkylsulphinyl or alkylsulphonyl each of up to 4 carbon atoms, or oxy or hydroxy substituents, or which if sufficiently saturated may bear one or two oxo substituents;
to provide a substituted dioxolanone having the following formula:

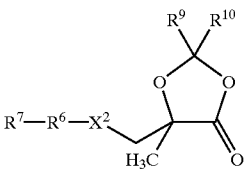

hydrolyzing the substituted dioxolanone to provide a free carboxylic acid compound having the following structure:

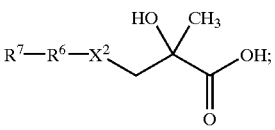

reacting the free carboxylic acid compound with a compound having the structure of Formula XIII:

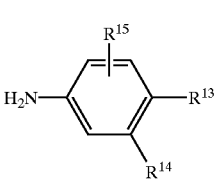

Formula XIII wherein
R$^{13}$ is cyano, carbamoyl, nitro, fluoro, chloro, bromo, iodo, or hydrogen, or alkyl, alkoxy, alkanoyl, alkylthio, alkylsulphinyl, alkylsulphonyl, perfluoroalkyl, perfluoroalkylthio, perfluoroalkylsulphinyl or perfluoroalkylsulphonyl each having up to 4 carbon atoms, or phenylthio, phenylsulphinyl or phenylsulphonyl;
R$^{14}$ is cyano, cabamoyl, nitro, fluoro, chloro, bromo or iodo, or alkanoyl, alkylthio, alkylsulphinyl, alkylsulphonyl, perfluoroalkyl, perfluoroalkylthio, perfluoroalkylsulphinyl or perfluoroalkylsulphonyl each having up to 4 carbon atoms; or phenylthio, phenylsulphinyl or phenylsulphonyl; and
R$^{15}$ is hydrogen or halogen;
to provide a compound having the structure of Formula XX:

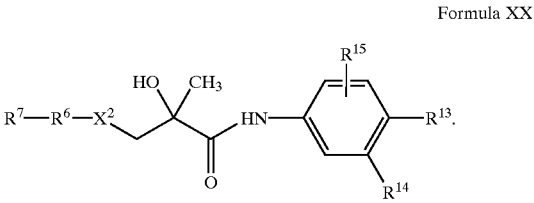

Formula XX

* * * * *

UNITED STATES PATENT AND TRADEMARK OFFICE
CERTIFICATE OF CORRECTION

PATENT NO. : 6,583,306 B1
DATED : June 24, 2003
INVENTOR(S) : Ekwuribe

It is certified that error appears in the above-identified patent and that said Letters Patent is hereby corrected as shown below:

Column 15,
Line 14, should read as follows: -- Synthesizing 4-Methyl-5-oxo-2-trihromomethyl-[1, --
Line 36, should read as follows: -- Synthesizing 5-Bromomethyl-5-methyl-2- --

Column 16,
Line 36, should read as follows: -- Synthesizing N-(4-cyano-3-trifluoromethyl-phenyl)- --

Column 17,
Line 41, should read as follows: -- perfluoroalkylthio, perfluoroalkylsulphinyl, --
Line 66, should read as follows: -- $R^{14}$ is cyano, carbamoyl, nitro, fluoro, chloro, bromo or --

Column 19,
Line 5, should read as follows: -- compound having the structure of Formula XXIII: --

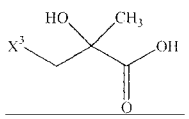

Column 21,
Line 17, should read as follows:
-- 24. The method according to claim 1, wherein $X^2$ is sul- --

Column 23,
Line 17, should read as follows:
-- 36. The method according to claim 35, wherein the --
Line 49, should read as follows:
-- 39. The method according to claim 38, wherein the --

Column 25,
Line 39, should read as follows:
-- $R^{11}$ is alkylene and $X^4$ is alkyl, halogen or aryl. --

Column 28,
Line 30, should read as follows:
-- $R^{14}$ is cyano, carbamoyl, nitro, fluoro, chloro, bromo or --

Column 29,
Line 1, should read as follows:
-- 65. The method according to claim 60, wherein $X^2$ is --

UNITED STATES PATENT AND TRADEMARK OFFICE
CERTIFICATE OF CORRECTION

PATENT NO. : 6,583,306 B1
DATED : June 24, 2003
INVENTOR(S) : Ekwuribe

It is certified that error appears in the above-identified patent and that said Letters Patent is hereby corrected as shown below:

Column 30,
Line 1, should read as follows:
-- $R^{14}$ is cyano, carbamoyl, nitro, flouro, chloro, bromo or --

Line 11, should read as follows: 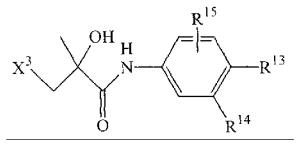

Column 32,
Line 40, should read as follows:
-- $R^{14}$ is cyano, carbamoyl, nitro, fluoro, chloro, bromo or --

Signed and Sealed this

Seventeenth Day of August, 2004

JON W. DUDAS
*Acting Director of the United States Patent and Trademark Office*